US009642318B2

(12) United States Patent
Gorguet et al.

(10) Patent No.: US 9,642,318 B2
(45) Date of Patent: May 9, 2017

(54) SEEDLESS PEPPER PLANTS

(71) Applicants: Benoit Gorguet, Avignon (FR); Carl M. Jones, Davis, CA (US); Dirk Vreugdenhil, s-Gravenzande (NL); Rebeca N. Benitez, Davis, CA (US)

(72) Inventors: Benoit Gorguet, Avignon (FR); Carl M. Jones, Davis, CA (US); Dirk Vreugdenhil, s-Gravenzande (NL); Rebeca N. Benitez, Davis, CA (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 1074 days.

(21) Appl. No.: 13/683,167

(22) Filed: Nov. 21, 2012

(65) Prior Publication Data
US 2013/0145489 A1    Jun. 6, 2013

Related U.S. Application Data
(60) Provisional application No. 61/562,942, filed on Nov. 22, 2011.

(51) Int. Cl.
*A01H 5/08* (2006.01)
(52) U.S. Cl.
CPC ..................................... *A01H 5/08* (2013.01)
(58) Field of Classification Search
None
See application file for complete search history.

(56) References Cited

U.S. PATENT DOCUMENTS

| | | | |
|---|---|---|---|
| 6,060,648 | A | 5/2000 | Heath |
| 7,728,194 | B2 | 6/2010 | Kim et al. |
| 2007/0180582 | A1 | 8/2007 | Kim et al. |
| 2010/0227041 | A1 | 9/2010 | Bar et al. |
| 2010/0333228 | A1* | 12/2010 | Shirai ..................... A01H 5/08 800/260 |
| 2013/0145489 | A1† | 6/2013 | Gorguet |

FOREIGN PATENT DOCUMENTS

| | | | |
|---|---|---|---|
| EP | 2245922 A1 | | 3/2010 |
| EP | 2245922 A1 † | | 11/2010 |
| EP | 25125522 A1 † | | 11/2010 |
| WO | WO 2004/099416 A1 | | 11/2004 |
| WO | WO 2008/013450 A1 | | 1/2008 |
| WO | 2008162134 A1 † | | 12/2008 |
| WO | WO 2008/152134 | | 12/2008 |
| WO | 2009098983 A1 † | | 8/2009 |
| WO | 2010011274 A1 † | | 9/2010 |
| WO | WO 2010/101274 | | 10/2010 |
| WO | WO 2012/087140 | | 6/2012 |

OTHER PUBLICATIONS

Shifriss (Euphytica, 93: pp. 83-88, 1997).*
Ishikawa et al., "High β-carotene and Capsaicinoid Contents in Seedless Fruits of 'Shishitoh' Pepper," *Hort Science* 39(1):153-155, 2004.
Schijlen et al., "RNA Interference Silencing of Chalcone Synthase, the First Step in the Flavonoid Biosynthesis Pathway, Leads to Parthenocarpic Tomato Fruits," *Plant Physiology* 144:1520-1530. 2007.
Tiwari et al., "Parthenocarpic potential in *Capsicum annuum* L. is enhanced by carpelloid structures and controlled by a single recessive gene," *BMC Plant Biology* 11:143, 2011.
European Extended Search Report for Application No. EP12851010, dated May 22, 2015.
Anand et al., "Functional male-sterility in *Capsicum annuum* L.," *Capsicum Newsletter IS* 7:32, 1988.
Andrasfalvy et al., "Cytoplasmic systems of interspecific hybrids in *Capsicum*, reconsidered," Eucarpia Vth Meeting on Genetics and Breeding of Capsicum and Eggplant, Plovdiv, Bulgaria, 1983.
Arrieta-Montiel et al., "Tracing evolutionary and developmental implications of mitochondrial stoichiometric shifting in the common bean," *Genetics* 158(2):851-64, 2001.
Bakker, The effect of temperature on flowering, fruit set and fruit development of glasshouse sweet pepper (*Capsicum annuum* L.) *J. Hort. Sci.* 64:313-320; 1989.
Berke, "Hybrid seed production in *Capsicum*," Journal of New Seeds 1:(3-4):49-67, 2000.
Bosland et al., "The genes of *Capsicum*," *HortScience* 41(5):1169-1187, 2006.
Charles et al., "Seedlessness in *Capsicum Annuum* L. var. Longum DC. (Sendt)," *J. Hort. Sci.* 54(2):159-162, 1979.
Csillery, "A contribution to the list of the possible interspecific crosses in *Capsicum*," Eucarpia V$^{th}$ Meeting on Genetics and Breeding of Capsicum and Eggplant, Plovdiv, Bulgary, pp. 15-17, 1983.
Dai et al., "Isozymes analyses of cytoplasmic male sterile (CMS) line in pepper (*Capsicum annuum* L.)," *Acta Botanica Boreali-Occidentalia Sinica* 27(9):1772-1776, 2007, abstract.
Gniffke et al., "Cytoplasmic male sterility in sweet pepper to produce hybrid seed," AVRDC Publication No. 09-718, AVRDC—The World Vegetable Center, Shanhua, Taiwan, pp. 1-12, 2009.

(Continued)

*Primary Examiner* — Brent Page
*Assistant Examiner* — Jared Shapiro
(74) *Attorney, Agent, or Firm* — Dentons US LLP; Matthew L. Madsen Esq.

(57) ABSTRACT

The present invention provides methods and composition for preparing seeds that when cultivated produce pepper plants with seedless fruits. These plants may further be male sterile and contain a stable non-Peterson Cytoplasmic Male Sterility ("CMS"). The invention also provides essentially pure populations of seed that, when grown, produce pepper plants with seedless fruit. Methods are provided comprising crossing a stable non-Peterson CMS plant as a female parent with pepper lines displaying a parthenocarpy trait. The invention also includes the seeds produced by such a method. Methods for breeding and using seedless pepper plants for enhancing the production of fruit under suboptimal temperature conditions are also provided.

22 Claims, 7 Drawing Sheets

(56) References Cited

OTHER PUBLICATIONS

Gulyas et al., "Altered transcript reveals an orf507 sterility-related gene in chili pepper (*Capsicum annuum* L.)," *Plant Molecular Biology Report* 28(4):605-612, 2010.
Hanson et al., "Mitochondrial gene organization and expression in petunia male fertile and sterile plants," *J Hered* 90(3):362-8, 1999.
Heuvelink et al., "Parthenocarpic fruit growth reduces yield fluctuation and blossom end rot in sweet pepper," *Ann. Bot.* 88:69-74, 2001.
Hu et al., "Breeding of Y92-1A, a cytoplasmic male sterility line of pepper," *Guizhou Agricultural Sciences* 8:13-14, 2009 (English abstract).
Janska et al., "Unusual mitochondrial genome organization in cytoplasmic male sterile common bean and the nature of cytoplasmic reversion to fertility," *Genetics* 135(3):869-79, 1993.
Janska et al., "Stoichiometric shifts in the common bean mitochondrial genome leading to male sterility and spontaneous reversion to fertility," *Plant Cell* 10(7)1163-80, 1998.
Jo et al., "Development of a CMS-specific marker based on chloroplast-derived mitochondrial sequence in peppers," *Plant Biotechnology Reports* 3:4, 2009.
Joshi et al., "Perspectives of bell pepper breeding," *Journal of New Seeds* 6(2-3): 51-74, 2005.
Kim et al., "Cleaved amplified polymorphic sequence and amplified fragment length polymorphism markers linked to the fertility restorer gene in chili pepper (*Capsicum annuum* L.)," *Mol Cells* 21(1):135-40, 2006.
Kim et al., "Isolation and characterization of the cytoplasmic male sterility-associated orf456 gene of chili pepper (*Capsicum annuum* L.)," *Plant Mol Biol* 63(4):519-32, 2007.
Kumar et al., "Validation of SCAR markers, diversity analysis of male sterile (S-) cytoplasms and isolation of an alloplasmic S-cytoplasm in *Capsicum*," *Scientia Horticulturae (Amsterdam)* 120(2):167-172, 2009.
Lee et al., "A CAPS marker linked to a genic male-sterile gene in the colored sweet pepper, 'Paprika' (*Capsicum annuum* L.)," *Breeding Science* 60(1):93-98, 2010.
Lee et al., "A CAPS marker associated with the partial restoration of cytoplasmic male sterility in chili pepper (*Capsicum annuum* L.)," *Molecular Breeding* 21(1):95-104, 2008.
Lee et al., "A codominant SCAR marker linked to the genic male sterility gene ($ms_1$) in chili pepper (*Capsicum annuum*)," *Plant Breeding* 129(1):35-38, 2010.
Lee et al., "Development of molecular marker linked to a genic male-sterile gene, $ms_k$ in chili pepper," *Korean Journal of Horticultural Science & Technology* 28(2):270-274, 2010 (abstract).
Lee et al., "Three AFLP markers tightly linked to the genic male sterility $ms_3$ gene in chili pepper (*Capsicum annuum* L.) and the conversion to a CAPS marker," *Euphytica* 173(1):55-61, 2010.
Lee et al., "Linkage analysis between the partial restoration (*pr*) and the restorer-of-fertility (*Rf*) loci in pepper cytoplasmic male sterility," *Theoretical and Applied Genetics* 117(3):383-389, 2008.
Liu et al., "Stability of AVRDC's cytoplasmic male sterile (CMS) pepper lines grown under low temperatures," *Capsicum and Eggplant Newsletter* 23:85-88, 2004.
Luo et al. "Male gamete development and early tapetal degeneration in cytoplasmic male-sterile pepper investigated by meiotic, anatomical and ultrastructural analyses," *Plant Breeding* 125:395-399, 2006.
Masuda et al., "Induced mutagenesis as a breeding strategy for improvement of solanaceous vegetables," *Gamma Field Symposia* 45:47-60, 2006.
Min et al., "Identification of a third haplotype of the sequence linked to the restorer-of-fertility (*RF*) gene and its implications for male-sterility phenotypes in peppers (*Capsicum annuum* L.)," *Molecules and Cells* 25(1):20-29, 2008.
Mulyantoro et al., "Modified complementation test of male sterility mutants in pepper (*Capsicum annuum* L.): preliminary study to convert male sterility system from GMS to CMS," *Euphytica* 169(3):353-361, 2009.

Nikornpun et al., "Morphological descriptors and male sterility in the genetic diversity of chilies (*Capsicum annuum* L.)," *Acta Horticulturae* 809:201-208, 2009.
Peterson, "Cytoplasmically inherited male sterility in *Capsicum*," *American Naturalist* 92:111-119, 1958.
Polowick et al., "Temperature effects on male-fertility and flower and fruit-development in *Capsicum annuum* L.," *Scientia Horticulturae* 25(2):117-127, 1985.
Pressman et al., "Influence of low night temperatures on sweet pepper flower quality and the effect of repeated pollinations, with viable pollen, on fruit setting," *J Hort. Sci. Biotechnol* 73(1):131-136, 1998.
Prolaram et al., "Seedless fruit mutant in *Capsicum*," *Capsicum Newsletter IS* 8-9:45-46, 1989.
Rylski et al., "Parthenocarpic fruit set and development in Cucurbitaceae and Solanaceae under protected cultivation in mild winter climate," *Acta Horticulturae* 287:117-126, 1991.
Shifriss et al., "An approach to parthenocarpy in peppers," *HortScience* 21(6):1458-1459 1986.
Shifriss et al., "Male sterility in pepper (*Capsicum annuum* L.)," *Euphytica* 93(1):83-88, 1997.
Tarchoun et al., "Differential parthenocarpy ability on selected local varieties of pepper grown in unheated greenhouse," *Capsicum and Eggplant Newsletter*, 18:32-35, 1999.
Tiwari et al., "Selection of sweet pepper (*Capsicum annuum* L.) genotypes for parthenocarpic fruit growth," *Acta Hort.* 761:135-140, 2007.
Tiwari, "Parthenocarpic fruit development in *Capsicum annuum*," Ph.D. Thesis, Wageningen University, 2011.
Wang et al., "QTL analysis of fertility restoration in cytoplasmic male sterile pepper," *Theor Appl Genet* 109(5):1058-63, 2004.
Wang et al., "RAPD analysis of genomic DNAs between CMS line of hot pepper and its maintainer line," *Acta Agriculturae Shanghai* 24(1):8-10, 2008 (English abstract).
Wang et al., "Genetic effects of the male sterile cytoplasmic gene in hot (sweet) pepper," *Acta Agriculturae Shanghai* 22(4):14-17, 2006 (English abstract).
Zou et al, "Effect of cytoplasmic male sterile genes on agronomic and biochemical characters in CMS lines and their $F_1$ hybrids in pepper," *Acta Horticulturae Sinica* 31(6):732-736, 2004 (English abstract).
Lee et al., "Study on identifying cytoplasmic male sterility (CMS) by DNA marker and associated CMS genes in peppers," Journal of the Taiwan Society for Horticultural Science 53(3):279-287, 2007. (English abstract at p. 287).
Liu et al., "ISSR marker of cytoplasmic male sterility in sweet pepper," Jiangsu Journal of Agricultural Sciences 25(3):607-609, 2009. (English abstract at p. 607).
Mackenzie, "The influence of mitochondrial genetics on crop breeding strategies," Plant Breeding Reviews 25:115-138, 2005.
Mackenzie, "The mitochondrial genome of higher plants: A target for natural adaptation," *Diversity and Evolution of Plants*. R. J. Henry. Oxon, UK., CABI 69-80, 2005.
Matlob et al., "Effect of growth regulators on parthenocarpic fruit development in tomato and pepper grown in the greenhouse," Emirates Journal of Food and Agricultural 3(1):1-9, 1991.
Molkhova et al., "Induction of Pepper (*Capsicum annuum* L.) Tetraploids and of Rediploids Arising From Them," Genetika i Selektsiya 21(1):27-30, 1988. (English abstract at p. 30).
Pathak et al., "Parthenocarpy in Chilies (*Capsicum annuum* L.)," *Capsicum and Genetics Newsletter* 102-103, 1993.
Pochard et al., "Haploid parthenogenesis in *Capsicum annuum* L.," *The Biology and Taxonomy of the Solanaceae* 455-472, 1979.
Saccardo et al., "Cytological investigation in the genus *Capsicum*," EUCARPIA III Meeting on Genetics and Breeding of Capsicum and Eggplant, Avignon-Montfavet, France, 1977.
Tofanelli et al., "Gibberellic acid on pepper parthenocarpic fruits production," Horticultura Basileiral 21(1):116-118, 2003. (English abstract at p. 116).
Wang et al., "Inheritance and distribution of fertility restoring gene of cytoplasmic male sterile pepper," ACTA Agriculturae Boreali-Sinica 22(1):86-89, 2007. (English abstract at p. 86).

(56) References Cited

OTHER PUBLICATIONS

Wei et al., "Studies on the characters and shape dissection of male sterile lines of pepper [*Capsicum annuum*]," *Journal of Shandong Agricultural University* 33(2):129-133, 2002. (English abstract at p. 129).

Yang et al., "Study on the superiority of hybrid breeding by male sterility in hot pepper," *J of China Capsicum* 1:36-38, 2008. (English abstract at p. 36).

International Search Report and Written Opinion of the International Searching Authority for International Appl. No. PCT/US2012/066268, dated Feb. 11, 2013.

Jankewicz et al., "Effect of growth regulators on parthenocarpic fruit set in *Capsicum annuum*," *Folia Horticulturae* 3(2):3-16, 1991.

Jayakaran et al., "Parthenocarpic fruit development in *Capsicum* by a morphactin," *Science and Culture* 39(4):188-189, 1973.

Kim et al., "The organization of mitochondrial atp6 gene region in male fertile and CMS lines of pepper (*Capsicum annuum* L.)," *Curr Genet* 49(1):59-67, 2005.

Kim et al., "Haplotype analysis of CMS-associated DNA markers in sweet peppers," *J. Crop Sci. Biotech* 12(3):129-134, 2009.

Lee et al., "Development of CAPS markers linked to St locus responsible for stability of cytoplasmic-genic male sterility in chili pepper (*Capsicum annuum* L.)," Poster presentation, PAA/Solanaceae, Jul. 25, 2006, Madison, WI.

Lee, "Development of AFLP marker linked to gene responsible for stable fertility in cytoplasmic-genic male sterility of chili pepper (*Capsicum annuum* L.)," Department Horticultural Science. Seoul, South Korea Seoul National University. MS: 57, 2003.

Moran, "Identifying maintainer (CMS B) lines in Chile," Presentation slides, New Mexico State University, Department of Agronomy and Horticulture, 2003.

Ravestijn, "Flower induction and improvement of fruit set in Capsicum," Groenten en Fruit 41(33):32-33, 35, 1986. English translation.

Satpute et al., "Seedlessness as a physiological parameter for enhanced pungency principle, a pharmaceutically useful quality trait, in Capsicum," abstract, Proc. of the XIIth Eucarpia Meeting on Genetics and Breeding of Capsicum and Eggplant, Noordwijkerhout, the Netherlands, 128,1004, May 17-19, 2004.

Shifriss et al., "Evaluating the parthenocarpic potential of peppers grown under summer conditions," Proc. of the VIIth Eucarpia Meeting on Genetics and Breeding of Capsicum and Eggplant, Kragujevac, Yugoslavia, 37-42, Jun. 27-30, 1989.

Dhaliwal et al., "Induction and exploitation of nuclear and cytoplasmic male sterility in pepper (Capsicum spp.): a review," *Journal of Horticultural Science & Biotechnology* 89(5):471-479, 2014.

Jan. 21, 2014 Amendment published by EPO 11 Pages.†

Shifriss,Male sterility in Pepper (*Capsicum annuum* L.), Euphytica pp. 83-88 1997 The Netherlands.†

Boukema, resistance to a new strain of TMV in Capsicum chacoense Hunz., 1982, Capsicum Newsletter 1, pp. 50-51 Turin, Italy.†

Tiwari, Parthenocarpic fruit development in Capsicum annuum, 117 pages, Wageningen University, 2011, The Netherlands.†

Johkan,M., Effect of Moderate Salinity Stress on the Sugar Concentration and Fruit Yield, in Single-truss, High-density, pp. 229-234, J. of japanese Horticultural Science, 2014.†

Luengwilai, Comparison of Leaf and Fruit Metabolism in Two Tomato (*Solanum lycopersicum* L.) Genotypes Varying in Total Soluble Solids, Journal of Agricultural and Food Chemistry (American Chemistry Society), 58(22).†

Heuvelink, E, 2001, Parthenocarpic Fruit Growth Reduces Yield Fluctuation and Blossom-end Rot in Sweet Pepper, Annals of Botany 88:69-74 (2001) (Oxford University Press) http://aob.oxfordjournals.org/content/88/1/69.full.pdf.†

Derera, Condiment paprika research in Australia, pp. 4-18, Journal of Business Chemistry (Germany), vol. 2, issue 1 2005.†

Gnifffke, Cytoplasmic male sterility in sweet pepper to produce hybrid Seed pp. 1-9 AVRDC Publication No. 09-718. 2009 Shanhua, Taiwan.†

Amendment of Sep. 12, 2014 published by USPTO.†

Amendment of Aug. 6, 2014 published by EPO.†

\* cited by examiner
† cited by third party

SEEDLESS PEPPER PLANTS

This application claims the priority of U.S. Provisional Appl. Ser. No. 61/562,942 filed Nov. 22, 2011, the entire disclosure of which is incorporated herein by reference.

BACKGROUND OF THE INVENTION

1. Field of the Invention

The present invention relates to the field of plant breeding and, more specifically, to the development of seedless pepper plants.

2. Description of Related Art

The goal of vegetable breeding is to combine various desirable traits in a single variety/hybrid. Production of hybrid peppers may be carried using genetic male sterility. Genetic male sterility in peppers can be obtained via two systems: a system in which the male sterility factors are coded in nuclear DNA ("genic;" "GMS"), or one in which the male sterility factors are coded in the mitochondrial DNA ("cytoplasmic;" "CMS"). Male sterility systems in which sterility is specified by a mitochondrial DNA trait, and in which fertility is restored by a nuclear trait are sometimes referred to as "CGMS"—Cytoplasmic—genic male sterility.

SUMMARY OF THE INVENTION

In one aspect, the invention provides a method for producing seed for growing a parthenocarpic seedless pepper plant comprising: crossing as a female parent a first pepper plant comprising a cytoplasmic male sterile (CMS) trait with a second plant which is parthenocarpic to produce at least a first seed of a parthenocarpic seedless pepper plant. In certain embodiments, the cytoplasm of a *C. baccatum* plant may be combined with the nuclear genome of a *C. annuum* plant by crossing plants; in other embodiments, the cytoplasm and nuclear genome may be combined by producing a somatic hybrid (e.g. by protoplast fusion). In one embodiment, the invention provides such a method wherein the CMS trait is not a Peterson CMS trait. In certain embodiments the CMS trait is derived from a *Capsicum baccatum* plant. The method may further comprise harvesting said seed. In some embodiments the method further comprises growing a parthenocarpic seedless pepper plant from said seed. One example of such a pepper plant is a bell pepper plant.

In some embodiments of the method the second pepper plant does not comprise a functional CMS restorer allele. In certain embodiment the method may further comprise producing a population of seeds of a parthenocarpic seedless pepper plant. In certain embodiments, 100% of the population of seeds produces a seedless pepper plant.

In another aspect, the invention provides a seed produced by crossing as a female parent a first pepper plant comprising a cytoplasmic male sterile (CMS) trait with a second plant which is parthenocarpic to produce at least a first seed of a parthenocarpic seedless pepper plant. A plant grown from such a seed, or a vegetative propagation thereof, is also provided by the invention, as well as a part of such a plant. Another aspect of the invention provides a method of producing a pepper plant comprising vegetatively propagating the plant. In some embodiments the plant part may further be defined as a leaf, a bud, a meristem, an embryo, a root, a root tip, a stem, a flower, a fruit, or a cell. In particular embodiments the plant part is further defined as a pepper fruit that lacks internal carpelloid structures.

A tissue culture of regenerable cells of such a parthenocarpic seedless pepper plant is another aspect of the invention, as is a population of seed produced by the disclosed methods, wherein 100% of the population of seed produces a seedless pepper plant.

In further embodiments, the invention provides seeds, plants and fruit prepared by a method of the invention. Populations of such plants, seeds and pepper fruits are also provided. In specific embodiments, the populations are defined as comprised of or consisting essentially of seedless pepper fruits, or seeds of plants, or plants that produce such seedless pepper fruits. In another embodiment, populations of pepper fruits are provided wherein at least about 80%, 90%, 95%, 99% or 100% of said population is made up of seedless pepper fruits. Populations of seed that produce plants with seedless pepper fruits and that are prepared by a method of the invention are also provided herein. Such populations may in specific embodiments be defined as comprised 100% of seed that produces seedless peppers. In certain embodiments the population may comprise at least about 25, at least about 50 or at least about 100 seeds. In still another embodiment, a pepper seed, plant or fruit in a composition or method of the invention is a bell pepper.

In another aspect, a method is provided for increasing the per plant yield of fruit of a sweet pepper plant, comprising growing plants produced from the seed of the pepper plant of claim 1 at a minimum daily temperature of 14° or under for at least 3 days during the growing period of flowering, pollination, and fruit set. Thus, a method is also provided for increasing the number or yield of fruit of pepper plants grown under cold conditions, comprising: growing a pepper plant comprising a parthenocarpy trait under cold conditions, and harvesting the fruit produced thereby. In one embodiment of the method, the pepper plant comprises a parthenocarpy trait and a CMS trait derived from *C. baccatum*.

Embodiments discussed in the context of methods and/or compositions of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF DRAWINGS

FIG. 6A: seeded yield is on the X axis and seedless yield on the Y axis. FIG. 6B: seeded versus seedless yield per scoring and on average. * indicates a significant difference between the two categories. The percentage of increase or decrease between seeded and seedless yield is also indicated.

DETAILED DESCRIPTION OF THE INVENTION

Figure 1:
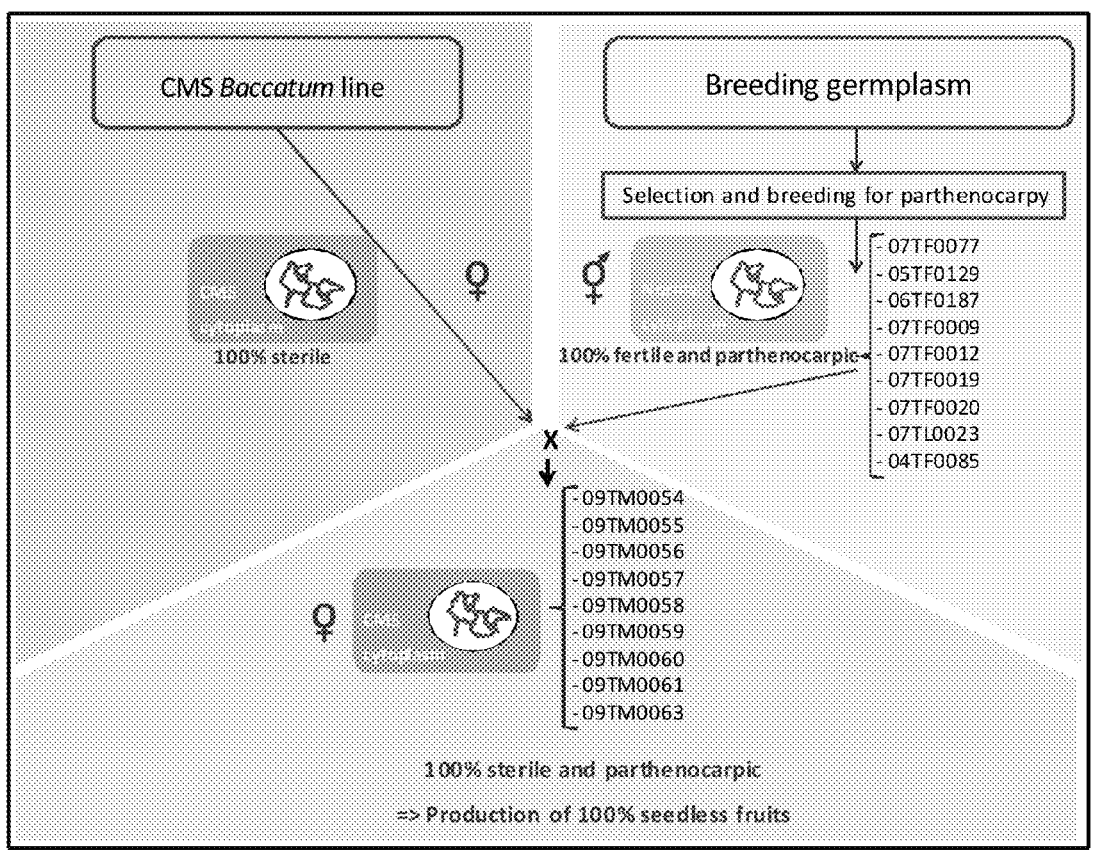
FIG. 1: Schematic presentation of the crossing for the development of seedless pepper plants. The non-Peterson CMS Baccatum line (line containing *C. baccatum* cytoplasm with *C. annuum* nuclear genome) is used as female plant and crossed with several cultivars of Corno di Toro (*C. annuum*) that were selected to be highly parthenocarpic, but male fertile. Progeny are cytoplasmic male sterile and parthenocarpic. Plants grown from the hybrid seed produce 100% seedless fruits.

The invention provides methods and compositions relating to pepper plants, seeds and derivatives of pepper plants/lines with a high level of parthenocarpy, and which produce seedless, or substantially seedless, fruit. In certain embodiments of the invention, the fruit of such plants are 100% seedless in that the fruit contain no viable seeds. The seedless peppers may be made in accordance with the invention by development and use of a pollinator line that displays a high level of parthenocarpy, and carries at least a first parthenocarpy gene. Such a line may be the result of direct selection in a breeding program for parthenocarpy, and more generally for seedless pepper. This line may then be crossed with, for example, an alloplasmic Cytoplasmic Male Sterile (CMS) pepper line. Additionally, genetic determinants found in the nucleus and cytoplasm may be combined by, for instance, protoplast fusion to produce a somatic hybrid plant with a cytoplasm from *C. baccatum* and a nuclear genome from *C. annuum*. In some embodiments, a pepper plant which produces seedless pepper fruit may be produced by one or more steps of sexual crossing and somatic hybridization according to methods well known in the art. The genetic basis for this alloplasmic CMS (i.e. this "CMS system") is distinct from the Peterson CMS system, and was found to be stable in all types tested to date, including in bell type and "Corno di Toro" types of peppers. In addition, no occurrence of restoration alleles in the breeding germplasm has been found in this CMS system. It was surprisingly found in particular that this system could be used in combination with parthenocarpy to obtain up to 100% yield of seedless pepper, with a general absence of restorer alleles and stability of the CMS system. The techniques described herein for yielding essentially pure populations of seed of a hybrid seedless pepper represent a major breakthrough for the future of seedless pepper, allowing for instance for production of seedless fruit of acceptable size on plants that do not suffer from irregular bearing ("flushing") of fruit.

Commercial peppers are primarily of the species *Capsicum annuum* (e.g. bell peppers), *Capsicum frutescens* (Tabasco pepper), *Capsicum chinense* (Habanero pepper), and *C. baccatum*. Pepper is an herbaceous annual species with fruits that vary in color, pungency and shapes and sizes. In view of the disclosed methods and compositions, pepper plants which produce seedless sweet fruit (lacking or having essentially undetectable levels of capsaicin), as well as seedless spicy fruit (containing capsaicin), of various shapes, colors, and sizes are contemplated, as well as (parental) seeds, cells, vegetative propagules, and fruit. For instance, the seedless fruit may be blocky or pointed, half-long, or of the Dulce Italiano or Corno di Toro types, among others.

Among *C. annuum* pepper plants, those pepper plants with bell-shaped or blocky fruits are termed "bell pepper" plants, that is pepper plants with a blocky fruit shape, wherein the fruit length divided by the fruit width is in a range from 0.8 to 1.2. These plants often have an irregular fruit set characterized by periods of high yield alternating with periods of low yield. This cyclical fluctuation of fruit set is known as "flushing." The observed fluctuation is explained by the competition for energy and assimilates between plant growth and fruit growth/fruit maturation. The presence of developing fruits is highly energy-consuming and is declining when the fruits are almost full-grown. A plant with both developing fruit and flowers will generally abort the flowers leading to a group of nodes without fruits. Flushing creates peaks in the market supply of peppers, which influences the market price of pepper. The labor demand in the greenhouses fluctuates equally with the availability of peppers. Growers thus prefer a more regular pattern of sweet pepper production.

The pepper Cytoplasmic Male Sterility ("CMS") system or Cytoplasmic Genic Male Sterility ("CGMS"), for which the male sterility factors are coded in the mitochondrial DNA, can be used for the production of fully male sterile progeny. The cytoplasm, including the mitochondria, is passed from the female parent to its progeny. Therefore the progeny plants coming from a cross between two parental plants, one used as female and one used as male, will carry the cytoplasm of the female parental plant. Therefore if this female parental plant displays the CMS trait, then it may be expected that all progeny will also carry that trait. This expectation of the CMS system is valid when both parental plants are deprived of so called "Restorer" alleles. In the presence of Restorer alleles, a plant will be fertile even if its cytoplasm is derived from a CMS maternal parent. For a long time, the only CMS system available in pepper was the Peterson CMS system. However the Peterson CMS system is unstable in many pepper types and most notably in the bell pepper type. Therefore when the Peterson CMS system is utilized for breeding with bell peppers, it is, to date, not useful for obtaining consistently seedless-fruited pepper plants.

Fertility restoration of Peterson's cytoplasmic male sterility in pepper is controlled by at least one major gene and several minor genes, and is thus variable in view of the genetic background of a given pepper plant. Fertility restoration is also environment-dependent. Restorer genes of the Peterson CMS system are widely spread in pepper, thus making the male sterile trait genetically unstable during breeding. Additionally, the Peterson CMS system is highly unstable at lower temperatures, such as below 24° C.

An alternate CMS system may thus be utilized, distinct from the Peterson CMS trait. Wide crosses were used to introgress the *C. annuum* nuclear genome into the cytoplasm of 3 species (*C. baccatum, C. frutescens* or *C. chacoense*). Backcrosses and marker assisted backcrossing were used to replace the nuclear genome of female parents of these species with a *C. annuum* nuclear genome, using marker-assisted screening and backcrosses to ensure the genome wide presence of *C. annuum* markers along every chromosome. The initial crosses were carried out with lines expected to be easier to cross with the other species, and the 09SP00004 line described below comprises a *C. baccatum* female pedigree (i.e. cytoplasm). $F_1$ progeny were confirmed as crosses with SSR markers and by phenotype. Any assayable genetic marker, e.g. in terms of its mapped location, may be used. SSR and SNP markers are well known in *Capsicum* including *C. annuum* (e.g. see Minamiyama et al., *Mol. Breeding* 18:157-169, 2006; Nagy et al., *Genome* 50:668-688, 2007; and Jung et al., *Euphytica* 175:91-107, 2010). Once $F_1$ progeny were established, selection was made in the early backcross generations for sterile plants, and these were backcrossed. After backcrossing, plants were evaluated for horticultural traits. In BC2 through BC4 generations SNP markers were used, distributed across the genome to select for the *C. annuum* genome. This method provides a rapid advance to the recurrent parent while eliminating the need to backcross plants to identify the more advanced lines by fruit types. The CMS trait in resulting lines was termed "*Baccatum* CMS."

The current invention thus provides methods in which a stable non-Peterson CMS system, such as *Baccatum* CMS, may be used in further breeding with a parthenocarpic pepper line, and which is demonstrated herein to yield progeny plants that are 100% male sterile and that produce seedless pepper fruit typically lacking even rudimentary carpelloid structures. Such methods may be carried out by crossing a female *Baccatum* CMS parent plant with a highly parthenocarpic male parent pepper plant. Various parthenocarpic pepper lines are known (e.g. CCA7234, CCA7235, and "Bruisma Wonder"; see also Shifriss and Eidelmann, *HortScience* 21:1458-1459, 1986; Tiwari et al., ISHS *Acta. Hort.* 761:135-140, 2007; Tiwari, "Parthenocarpic fruit development in *Capsicum annuum*. Ph.D. thesis, Wageningen Univ., 2011; US20100227041A1; and Gniffke et al., *AVRDC Publication No.* 09-718, Shanhua, Taiwan, 2009).

One such non-limiting example of a CMS *Baccatum* line is 09SP0004 (derived from female parent *C. baccatum* PI 159242 available from USDA-ARS GRIN, National Plant Germplasm System, Beltsville, Md. USA), which is listed in Table 2 and was used as the female parent for the production of the described seedless pepper fruit hybrid plants. Other female lines such as PI 497974 may also be utilized, for instance as described in Example 1. The CMS *Baccatum* trait may further be readily derived from other lines in addition to those listed in Table 2. Likewise, the CMS *Baccatum* trait could be introgressed into other lines, for instance by use of marker-assisted selection. The invention thus provides, in one embodiment, a pepper plant comprising the CMS trait found in pepper line 09SP0004.

The presence of a seedless trait, for instance in Solanaceous plants such as pepper, may also result in beneficial effects on fruit setting under cold conditions, fruit yield under cold conditions, and on Brix levels of fruit. That is, a significantly higher Brix (e.g. 1 point) may be seen.

As used herein, "cold conditions" is defined as a daily minimum temperature of less than 16° C., 14° C., 12° C., 10° C., 8° C. or 6° C. over a period of at least 3, 5, 7, 9 or more days, for instance during the period(s) of flowering, pollination, fruit setting, and fruit development and growth.

As used herein, "parthenocarpy" is defined as the development of fruits in absence of pollination and/or fertilization, results in the development of seedless fruits. Parthenocarpic fruit development may potentially improve the setting of the pepper fruits, particularly under cold growing conditions.

As used herein, "cytoplasmic male sterility" refers to plants that are not usually capable of breeding from self-pollination, but are capable of breeding from cross-pollination.

As used herein, a "female parent" refers to a pepper plant that is the recipient of pollen from a male donor line, which pollen successfully pollinates an egg. A female parent can be any pepper plant that is the recipient of pollen. Such female parents can be male sterile, for example, because of genic male sterility, cytoplasmic male sterility, or because they have been subject to manual emasculation of the stamens. Genic or cytoplasmic male sterility can be manifested in different manners, such as sterile pollen, malformed or stamenless flowers, positional sterility, and functional sterility.

As used herein, "male parent plant" refers to a parent plant that provides pollen to (i.e. is a pollinator for) a female line. They may be useful for breeding of progeny pepper plants, such as parthenocarpic seedless progeny plants.

As used herein, a "part of the pepper plant" is further defined as pollen, an ovule, a leaf, an embryo, a root, a root tip, an anther, a flower, a fruit, a stem, a cutting, a shoot, a seed, a protoplast, a cell, and a callus. A tissue culture of cells from a pepper plant may also be of use in propagating pepper plants of the present invention. As used herein, "tissue culture" refers to a composition comprising isolated cells of the same type(s) or of a different type, or of a collection of such cells, that may be organized into parts of a plant.

As used herein, a "hybrid pepper plant" includes a plant resulting directly or indirectly from crosses between populations, breeds or cultivars within the genus *Capsicum*. "Hybrid pepper plant" as used herein also refers to plants resulting directly or indirectly from crosses between different species, varieties or genotypes.

As used herein, a "marker" is an indicator for the presence of at least one phenotype, genotype, or polymorphism. Markers include, but are not limited to, single nucleotide polymorphisms (SNPs), cleavable amplified polymorphic sequences (CAPS), amplified fragment length polymorphisms (AFLPs), restriction fragment length polymorphisms (RFLPs), simple sequence repeats (SSRs), insertion(s)/deletion(s) ("INDEL"(s)), inter-simple sequence repeats (ISSR), and random amplified polymorphic DNA (RAPD) sequences. A marker is preferably inherited in codominant fashion (both alleles at a locus in a diploid heterozygote are readily detectable), with no environmental variance component, i.e., heritability of 1. A "nucleic acid marker" as used herein means a nucleic acid molecule that is capable of being a marker for detecting a polymorphism, phenotype, or both associated with a trait of interest. Stringent conditions for hybridization of a nucleic acid probe or primer to a marker sequence or a sequence flanking a marker sequence refers, for instance, to nucleic acid hybridization conditions of 1×SSC, and 65° C. As used herein, "marker assay" means a method for detecting a polymorphism at a particular locus using a particular method, e.g. measurement of at least one phenotype (such as a visually detectable trait, including disease resistance), restriction fragment length polymorphism (RFLP), single base extension, electrophoresis, sequence alignment, allelic specific oligonucleotide hybridization (ASO), random amplified polymorphic DNA (RAPD), microarray-based technologies, PCR-based technologies, and nucleic acid sequencing technologies, etc.

Many useful traits that can be introduced by backcrossing, as well as directly into a plant, are those which are introduced by genetic transformation techniques. Genetic transformation may therefore be used to insert a selected transgene into a plant of the invention or may, alternatively, be used for the preparation of transgenes which can be introduced by backcrossing. Methods for the transformation of plants that are well known to those of skill in the art and applicable to many crop species include, but are not limited to, electroporation, microprojectile bombardment, *Agrobacterium*-mediated transformation and direct DNA uptake by protoplasts. Exemplary nucleic acids which may be introduced to plants of this invention include, for example, DNA sequences or genes from another species, or even genes or sequences which originate with or are present in the same species, but are incorporated into recipient cells by genetic engineering methods rather than classical reproduction or breeding techniques.

One aspect of the current invention thus concerns methods for producing seed for pepper hybrids that grow to yield parthenocarpic seedless fruit. Plants of a female pepper parent displaying the *Baccatum* CMS trait, such as *C. baccatum* 09SP0004 may be used in certain embodiments for the development of new parthenocarpic seedless pepper varieties, for instance via marker assisted selection. Alternatively or in addition, a pepper CMS line may be developed by introgressing the *C. annuum* nuclear genome into cytoplasm from another *Capsicum* such as *C. frutescens*, or *C. chacoense*, including via marker assisted backcrossing to assess replacement of the nuclear genome of any of these three species, or another *Capsicum*, with a nuclear genome from *C. annuum*.

The development of new varieties using one or more starting varieties is well known in the art. Genetic marker may be utilized in a marker assisted selection breeding method to create novel parthenocarpic lines or cultivars. Alternatively other parthenocarpy-associated genetic markers may be identified by a skilled worker, and may be utilized in accordance with the invention. Thus novel varieties may be created by crossing a stable CMS line, such as a *Baccatum* CMS line such as 09SP0004, with a parthenocarpic line followed by evaluation of fruiting characteristics of progeny plants. In particular, when a parthenocarpic pepper line is crossed with the CMS *Baccatum* as described herein, the level of parthenocarpy in the F1 generation can be evaluated because the F1 will be male sterile. Thus the fruit produced will be seedless.

To evaluate the level of parthenocarpy in the F1 generation [CMS *Baccatum*×parthenocarpic line], a person skilled in the art can measure the number of fruit setting on the plants, as well as, optionally, measure the size of the fruit (length and width), and compare those measurements with ones obtained upon hand pollination of the same F1 genotypes which would yield seeded fruit.

If the level of parthenocarpy obtained in the F1 is not sufficient, one may perform a cross between the original parthenocarpic fertile line and another parthenocarpic line to obtain an F1 generation and subsequently self these F1's. The obtained F2's can be crossed to a CMS *Baccatum* line in order to assess their level of parthenocarpy when combined with CMS *Baccatum*. If the level of parthenocarpy appears useful, an F2 plant may be selfed down to, for instance, an F5 or F6 generation in order to genetically fix these genotypes. At each self generation an additional round of selection for parthenocarpy (and other agronomic trait(s)) can be done by crossing a set of plants of a specific generation to a pepper line exhibiting the CMS *Baccatum* trait, eventually selecting plants which give a desired level of parthenocarpy in combination with the CMS *Baccatum* trait.

In the present invention, out of 9 F1 hybrids generated by crossing parthenocarpic pepper lines with a CMS *Baccatum* trait-exhibiting line, 8 gave a satisfactory level of parthenocarpy in the F1, and only one did not. Thus, a person skilled in the art, using the parthenocarpic material available in the literature, can successfully obtain a further parthenocarpic line when crossing a parthenocarpic line with a line exhibiting a CMS *Baccatum* trait.

New varieties may be created by crossing with a second plant of a male parental line which is parthenocarpic. In selecting such a second plant to cross for the purpose of developing novel lines, it may be desired to choose those plants which either themselves exhibit one or more selected desirable characteristics or which exhibit the desired characteristic(s) when in hybrid combination. Once crosses have been made, selection may take place to identify new varieties which, if seedless, may be propagated vegetatively, including via well known tissue culture techniques. Alternatively, CMS lines may be propagated via pollination by another (fertile) genotype to obtain seed.

The plants of the present invention are particularly well suited for the development of new lines based on the nature of the genetic background of the plants, particularly in view of the CMS and parthenocarpy traits of the parental lines, which may be indicative of suitability of use in a method of producing seeds capable of growing into a seedless pepper plant, as well as other agronomically useful traits listed below. In selecting a second plant to cross with a *Baccatum* CMS line for the purpose of developing novel pepper lines, it may typically be preferred to choose those plants which either themselves exhibit one or more selected desirable characteristics or which exhibit the desired characteristic(s) when in hybrid combination. Examples of desirable traits may include, in specific embodiments, parthenocarpy, high seed yield, high seed germination, seedling vigor, high fruit yield, disease tolerance or resistance, and adaptability for soil and climate conditions. Consumer-driven traits, such as a fruit shape, color, texture, and taste are other examples of traits that may be incorporated into new lines of pepper plants developed by this invention. As described, seedless and parthenocarpic progeny of female line 09SP0004 exhibit desirable agronomic traits. For instance, the characteristics of fruit from representative lines 09TM0054, 09TM0055, 09TM0056, 09TM0057, 09TM0058, 09TM0059, 09TM0060, 09TM0061, and 09TM0063 were the subject of an objective analysis for size, seedlessness, and presence of carpelloid structures.

Deposit Information

A deposit of pepper line 09SP0004, which is disclosed herein above and referenced in the claims, was made with the American Type Culture Collection (ATCC), 10801 University Blvd., Manassas, Va. 20110-2209. The date of deposit was Oct. 21, 2011 and the accession number for those deposited seeds of pepper line 09SP0004 is ATCC Accession No. PTA-12179. All restrictions upon the deposit have been removed, and the deposit is intended to meet all of the requirements of 37 C.F.R. §1.801-1.809. The deposit will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

EXAMPLES

Example 1

Generation of CMS *Baccatum* Lines

The pepper plants/lines used as the females in the seedless pepper plants described herein below, of the type "Corno di Toro", were developed by introgressing the *C. annuum* nuclear genome into cytoplasm from *C. baccatum, C. frutescens*, or *C. chacoense* via marker assisted backcrossing to replace the nuclear genome of the three latter species with a nuclear genome from *C. annuum*. The marker assisted backcrossing strategy utilized markers along each pepper chromosome to assess the extent of replacement of the nuclear genome in given tested plants with that of the recurrent parent.

Creation of interspecific F1 plants was accomplished by emasculating flowers of *C. baccatum, C. frutescens* or *C. chacoense* in early morning before the anthers had shed their pollen. Pollination with pollen of *C. annuum* was done around 10 AM. 200 mg/l NAA (1-napthylacetic acid) was applied onto pollinated flowers 1 day post-pollination by dipping the whole flower into a microcentrifuge tube containing the growth regulator solution. When the growth regulator dried up, a second pollination with the same pollen was applied. Fruit were harvested when ripe and seed extraction and embryo rescue were done under aseptic conditions. Embryos were dissected from endosperms and cultured on MS (Murashige & Skoog) media until seedlings were fully developed. *C. annuum* nuclear genome donor lines (i.e. pollen parents) "A"-"N" are listed in Table 1. Production of interspecific F1 plants is summarized in Table 2.

TABLE 1

| *C. annuum* male parent lines | | |
|---|---|---|
| Code | Line designation | Description |
| A | P3117 (PI 640666) | Asian |
| B | P3850 (PI 640488) | P3850 |
| C | L633 | L633 |
| D | P63 | Cherry Sweet |
| E | P599 | P599 |
| F | P65 | CM334 |
| G | HP 470 | Asian |
| H | HAP 114-1008 | Ancho |
| I | AP1748 | Bell/Blocky |
| J | SJR 114-1016 | Jalapeño |
| K | PX 1141-0025 | TMV R Hybrid |
| L | PS2391 | TMV R Hybrid |

TABLE 2

| Production of interspecific F1 plants. | | | | | |
|---|---|---|---|---|---|
| *Capsicum* Species (female donor) | Generation | Cytoplasm Donor lines | Nuclear Genome Donors (see Table 1) | Phenotype | Selection Method |
| baccatum | F$^1$ | PI 497974, PI 159242, PI 640880 | A, B, C, D, E, F | All sterile | Phenotypic (sterility) |
| baccatum | BC$^1$ | PI 497974, PI 159242, PI 640880 | A, G, H, I, J | All sterile | Phenotypic (sterility) |
| baccatum | BC$^2$ | PI 497974, PI 159242, PI 640880 | A, G, H, I, J | All sterile (some families had some very limited fertility) | Phenotypic (sterility and fruit size) |
| baccatum | BC$^3$ | PI 497974, PI 159242, PI 640880 | I, J | All sterile | Background selection with markers (384 plex) |
| baccatum | BC$^4$ | PI 497974, PI 159242, PI 640880 | I, J | All sterile | Background selection with markers (192 plex) |
| chacoense | F$^1$ | PI 260429 | C, D, E, F, I | All sterile | Phenotypic (sterility) |
| chacoense | BC$^1$ | " | A, G, H, I, J | All sterile | Phenotypic (sterility) |
| chacoense | BC$^2$ | " | G, H, I, J | All sterile | Phenotypic (sterility and fruit size) |
| chacoense | BC$^3$ | " | I, J | All sterile | Background selection with markers (384 plex) |

TABLE 2-continued

Production of interspecific F1 plants.

| Capsicum Species (female donor) | Generation | Cytoplasm Donor lines | Nuclear Genome Donors (see Table 1) | Phenotype | Selection Method |
|---|---|---|---|---|---|
| chacoense | BC$^4$ | " | I | All sterile | Background selection with markers (192 plex) |
| frutescens | F$^1$ | PI 1594141 | K, L | Fertile | Phenotypic (sterility) |
| frutescens | BC$^1$ | " | G, H, I, J | Fertile | Phenotypic (sterility and fruit size) |
| frutescens | BC$^2$ | " | I, J | All families segregating fertile/sterile | Background selection with markers (384 plex) |
| frutescens | BC$^3$ | " | I, J | All families segregating fertile/sterile | Background selection with markers (192 plex) |

Interspecific F1 progeny were confirmed with SSR markers selected to assess the entire pepper genome, and by phenotype. Such marker-assisted background selection may utilize SSR, SNP, and other genetic markers known in the art. Once the F1 progeny were established, selection in the early backcrosses was based on horticultural traits, in particular the male sterility trait. Male sterile F1 and backcross plants were grown in the greenhouse and pollinated with pollen from various *C. annuum* nuclear genome donors as listed in Table 2.

Male sterile plants were further backcrossed with *C. annuum*. In BC2 through BC4 generations SNP markers across the genome were used to select for the *C. annuum* genome, allowing for a rapid advance in achieving the traits of the recurrent parent and reducing the number of backcrosses needed. The selected CMS *Baccatum* line was designated 09SP0004 and is derived from PI 159242. Alternatively, another *Baccatum* line may be utilized. 09SP0004 can be crossed with a variety of lines without the sterility being restored by nuclear genes present in the male parent of a cross or in recurrent parents during a CMS conversion. This is in contrast to the Peterson CMS/Rf system which can be restored in this way. This new CMS system has a very low occurrence of restoration alleles in the breeding germplasm. The new CMS system developed is stable in all types tested to date, which includes the bell type "Como di Toro." The CMS *Baccatum* line 09SP0004, listed in Table 3, was used as the female parent for the production of the described seedless pepper fruit hybrid plants, although any other female lines with similar traits may also be utilized.

Example 2

Development of Pepper Lines Displaying a High Level of Parthenocarpy

Figure 2:
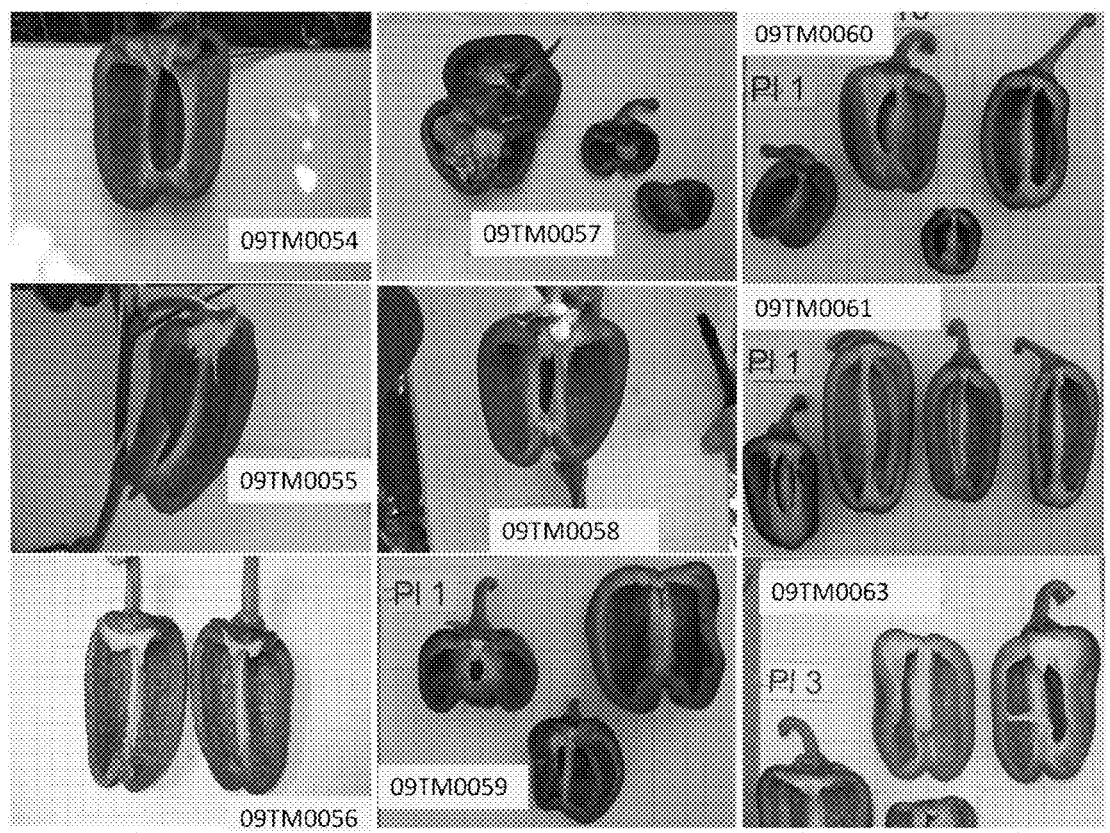
FIG. 2: Fruits of the progeny from the cross non-Peterson CMS Baccatum and the selected cultivars of Corno di Toro that are highly parthenocarpic. Depicted are representative fruits of the progeny. The fruits were cut open and put on a 1 cm paper grid.

A set of 9 lines was selected for their high level of parthenocarpy observed in absence of pollination, as indicated under "Male Parent" in Table 3. A high level of parthenocarpy is defined by regular fruit set in absence of pollination independent of the environmental conditions. The fruits growing in absence of pollination are of attractive size and shape from a consumer perspective. The crossing scheme of the present invention is described in FIG. 1. As shown in FIG. 2 and below, the fruits of progeny plants obtained following the crossing of a *Baccatum* CMS line with parthenocarpic pollinators do not contain, or contain only limited, internal growth structures referred as internal carpelloid structure (Tiwari et al, *Acta Hort.* 761:135-140, 2007). None of the plants produced seed.

TABLE 3

Line codes of plant material

| Female parent | Male Parent | Progeny |
|---|---|---|
| 09SP0004 | 07TF0077 | 09TM0054 |
| 09SP0004 | 05TF0129 | 09TM0055 |
| 09SP0004 | 06TF0187 | 09TM0056 |
| 09SP0004 | 07TF0009 | 09TM0057 |
| 09SP0004 | 07TF0012 | 09TM0058 |
| 09SP0004 | 07TF0019 | 09TM0059 |
| 09SP0004 | 07TF0020 | 09TM0060 |
| 09SP0004 | 07TL0023 | 09TM0061 |
| 09SP0004 | 04TF0085 | 09TM0063 |

Example 3

Evaluation of Fruit Characteristics in Progeny Plants

Figure 3:
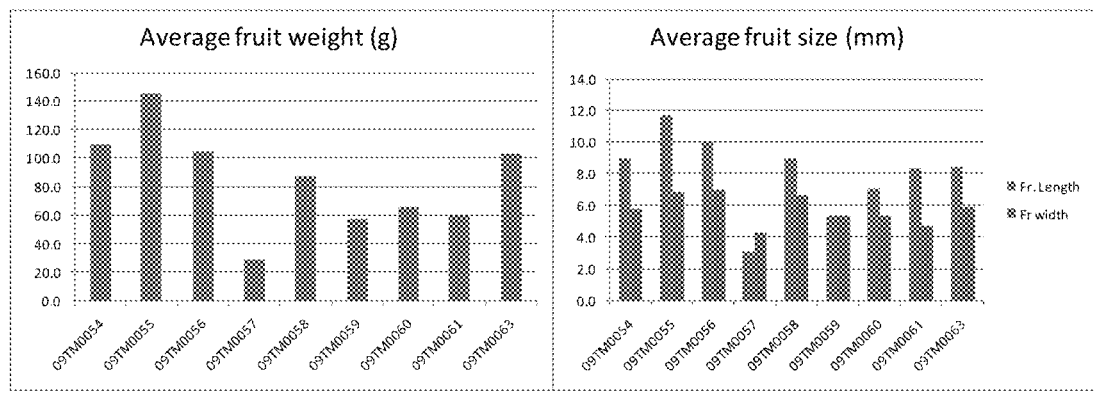
FIG. 3: Plot of average fruit weight and size of progeny fruit. Graphical representation of average fruit weights of progeny fruit (in grams) and of the length and width (in millimeter).

The progenies obtained by crossing the CMS *Baccatum* line with the parthenocarpic lines, were grown to maturity and fruit were obtained. Table 4 summarizes the fruit measurements recorded from the progeny plants listed in Table 3. Fruit of the progeny were randomly collected and evaluated for fruit weight, width, length, and presence of seeds and internal structures. Representative fruit are depicted in FIGS. 2-3. The fruit did not contain any seeds, which demonstrates that the male sterility is stable under typical growing conditions. Among the progeny plants, 09TM0055 had the highest level of production in terms of fruit size and regularity of setting. Progeny line 09TM0057 produced fruit of small size and with internal carpelloid structures. Fruit set was considered regular, without undue "flushes" of production.

TABLE 4

Summary of size measurements from fruit of seedless lines.

| Line code. | # fruits measured | Average Fruit weight (g) | Average Fruit size (mm) Length | Width | Seed content | Internal Carpelloid |
|---|---|---|---|---|---|---|
| 09TM0054 | 9 | 109.6 | 9.0 | 5.8 | no | no |
| 09TM0055 | 13 | 144.8 | 11.7 | 6.9 | no | <3 cm3 |
| 09TM0056 | 2 | 105.0 | 10.0 | 7.0 | no | no |
| 09TM0057 | 20 | 28.8 | 3.1 | 4.3 | no | ~3 cm3 |
| 09TM0058 | 9 | 87.5 | 9.0 | 6.6 | no | no |
| 09TM0059 | 7 | 57.5 | 5.4 | 5.4 | no | no |
| 09TM0060 | 12 | 65.8 | 7.1 | 5.4 | no | no |
| 09TM0061 | 13 | 59.5 | 8.3 | 4.7 | no | no |
| 09TM0063 | 7 | 103.3 | 8.4 | 5.9 | no | no |

Example 4

Use of Seedless Peppers to Improve Setting Under Cold Conditions

Twenty pepper genotypes were selected to study the effect of seedlessness on setting of fruit under cold conditions. Of these, 17 lines were segregating for GMS and 3 were segregating for CMS. The trial was organized as an RCBD with 4 repetitions; with 5 sterile and 5 fertile plants per plot. 32 seedlings per genotype per rep were tested with the GMS marker prior to planting. CMS plants were all sterile and were therefore not subjected to marker screening. The trial was sown on July 15 in the greenhouse. Leaf samples were tested for marker screening by August 5th. The trial contained 736 plants since for some of the genotypes as many as 5 sterile and 5 fertile plants per plot were not available. Temperature data were recorded inside the greenhouse compartment. Three harvests were performed, with $1^{St}$ scoring on December 12th for nodes 0, 1, 2, 3; $2^{nd}$ scoring on January 18 for nodes 4, 5, 6, 7; and $3^{rd}$ scoring on March 1 for nodes 8, 9, 10, 11. At each scoring, the following traits were scored on every single plant: fruit number (excluding button fruit); button fruit number; total fruit weight (g); fruit length (cm); fruit width (cm); presence/absence of seeds; and the derived trait of single fruit weight (g). Statistical analysis was performed with JMP analysis software (SAS Software, Cary, N.C., USA). No significant interaction between the sterility status and the repetitions were observed for the measured traits. To correct the analysis for the differences in fruit types/sizes across the different pedigrees, the pedigrees were analyzed as a random effect in the ANOVAs.

Figure 4:
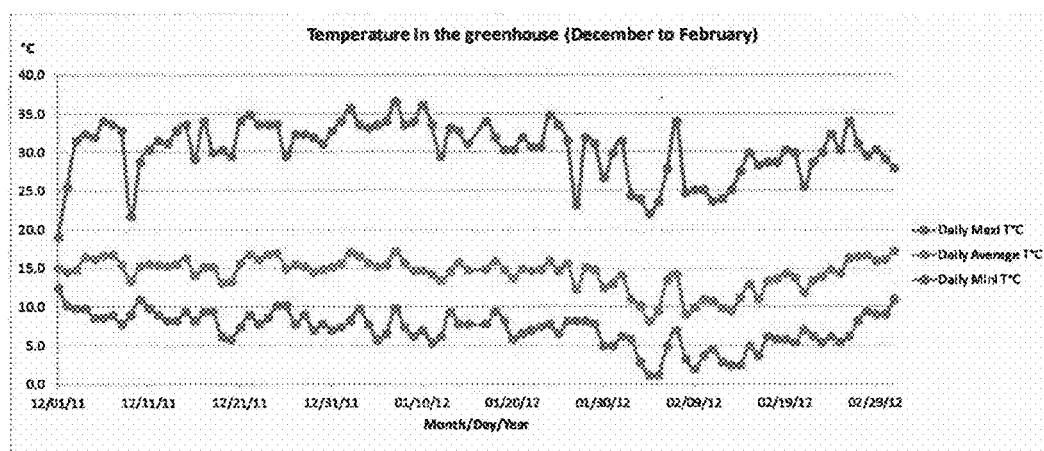
FIG. 4: Greenhouse temperature data as discussed in Example 4.
Figure 5:
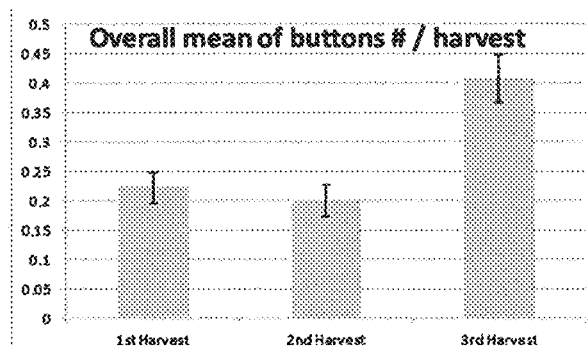
FIG. 5: Mean number of button fruit at each harvest time.

Temperature data were recorded inside the greenhouse compartment for the period of Dec., Jan. and Feb. which coincides with the cold period (FIG. 4). The minimum daily temperature was consistently below 12° C. during that period. In pepper, the formation of malformed fruit is associated with low temperature during pollination. Flattened fruit or "buttons" indicate insufficient pollination (Pressman et al., J. Hortic. Sci. Biotechnol. 73:131-136, 1998). The functioning of female flower organs is inhibited at low night temperatures (14° C. or less) which gives rise to flattened fruit. The optimum temperature for flowering and fruit set in pepper is about 16° C. (Pressman et al., 1998), while the optimum 24-hour temperature for yield is about 21° C. To identify the period at which the trial entered cold stress, setting of button fruit across the three harvesting dates (FIG. 5) was analyzed. Button setting increased from the second to third harvest which indicates that the climatic conditions (i.e. mean temperature) were likely sub-optimal for fruit set.

Fruit weight, number, length, and width were analyzed for fertile and sterile plants (Tables 5-6). The weight of fruit strongly correlated with the width of fruit, which is in accordance with what has been observed in other trials. The number of fruits is negatively correlated with the mean width and the mean weight of fruit, which is also in accordance with what has been observed in other trials.

TABLE 5

Correlations on fertile plants

|  | fruits weight per scoring | fruit number per scoring | Mean length of fruit (cm) | Mean width of fruit (cm) | Mean weight of fruit (g) |
|---|---|---|---|---|---|
| fruit weight per scoring | 1.00 | 0.01 | 0.10 | 0.51 | 0.57 |
| fruit # per scoring | 0.01 | 1.00 | 0.08 | −0.73 | −0.71 |
| Mean length of fruit (cm) | 0.10 | 0.08 | 1.00 | −0.24 | −0.15 |
| Mean width of fruit (cm) | 0.51 | −0.73 | −0.24 | 1.00 | 0.92 |
| Mean weight of fruit (g) | 0.57 | −0.71 | −0.15 | 0.92 | 1.00 |

TABLE 6

Correlations on sterile plants

|  | fruits weight per scoring | fruit number per scoring | mean length of fruit (cm) | mean width of fruit (cm) | Mean weight of fruit (g) |
|---|---|---|---|---|---|
| fruit weight per scoring | 1.00 | 0.25 | 0.18 | 0.42 | 0.34 |
| fruit # per scoring | 0.25 | 1.00 | 0.18 | −0.61 | −0.66 |
| Mean length of fruit (cm) | 0.18 | 0.18 | 1.00 | −0.25 | −0.07 |
| width of 1 fruit (cm) | 0.42 | −0.61 | −0.25 | 1.00 | 0.76 |
| Mean weight of fruit (g) | 0.34 | −0.66 | −0.07 | 0.76 | 1.00 |

Figure 6A:
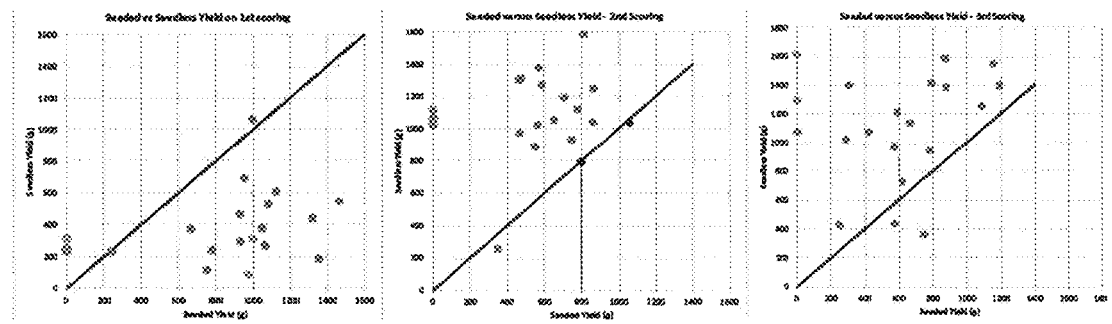
FIGS. 6A-6B: Fruit yield of seeded vs. seedless plants at each harvest time.
Figure 6B:
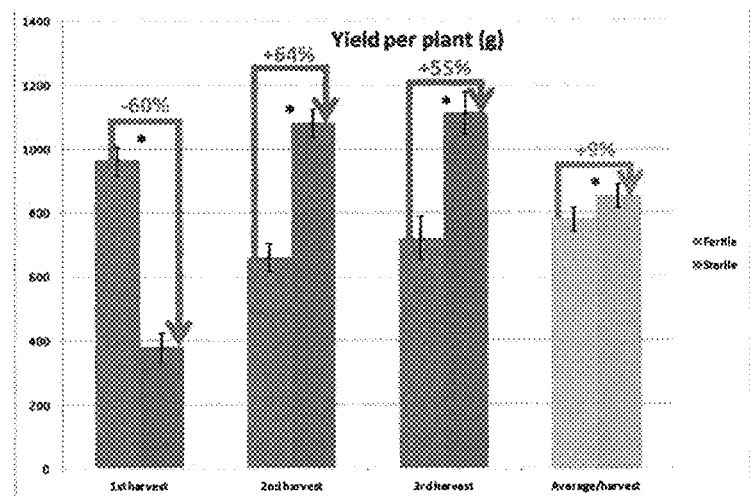

Yield per plant on seeded versus seedless plants per harvest/scoring was analyzed (FIGS. 6A-6B). Yield performance differed significantly (p<0.0001) on seeded versus seedless plants between the first scoring and the two subsequent scorings. In the first scoring, the yield obtained on seedless plants was significantly lower than on seeded plants. On the second and third scorings, the seedless plants yielded significantly more than the seeded plants. This contributed to an overall significantly higher yield on seedless plants than on seeded plants by 9%. When looking within seeded plants, a decrease of yield from the first to the second scoring was seen, likely due to the flushing effect. The third scoring did not recover the level of production observed on the first scoring, perhaps because of the cold conditions as suggested by the increased number of buttons. Yield on the CMS plants (for which the comparison with seeded versions was not performed) showed a similar yield trend as that of the GMS genotype plants, which indicates that use of a CMS sterility system also appears appropriate for these growing conditions.

Figure 7:
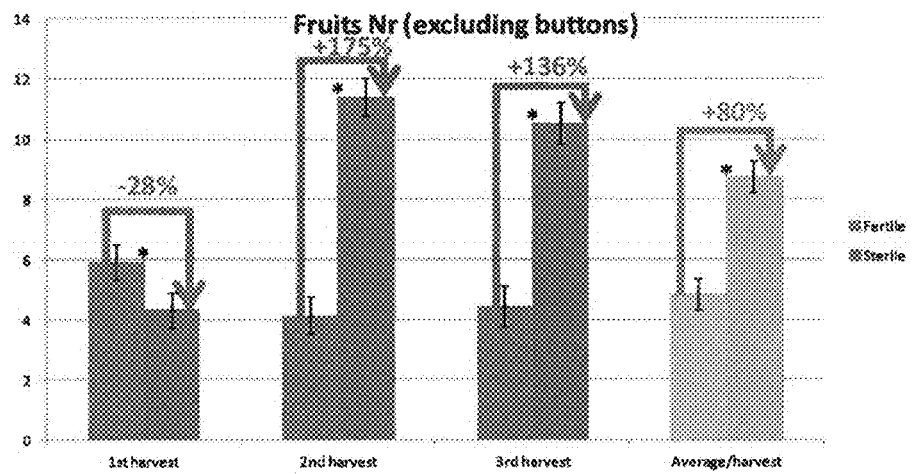
FIG. 7: Number of fruit on seeded versus seedless plants, per plant per scoring and on average over the three harvest dates. * indicates a significant difference between the two categories. The percentage of increase or decrease between seeded and seedless fruit numbers is also indicated.

Fruit number per plant was also examined. Fruit number per plant followed the same trend as yield per plant. A significantly lower number of fruits in the first scoring on seedless versus seeded plants was seen, followed by a higher number of fruits in the second and third scoring on seedless versus seeded plants. Overall the seedless plants produce 80% more fruits than the seeded plants (FIG. 7).

Figure 8:
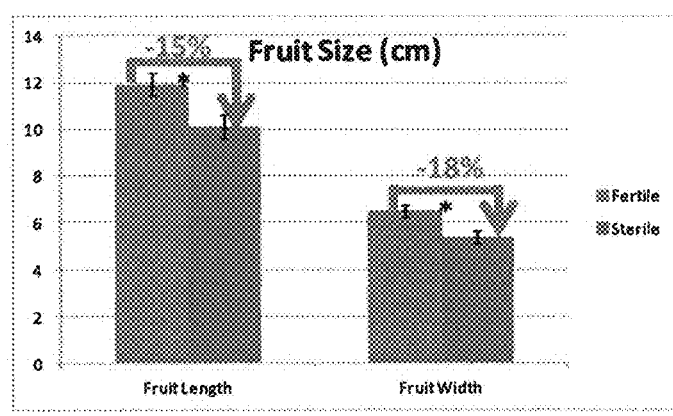
FIG. 8: Fruit size analysis for seeded versus seedless fruit. * indicates a significant difference between the two categories. The percentage of decrease between seeded and seedless fruit size is also indicated.

Fruit size and weight were examined for seeded vs. seedless plants. Seedless fruits were significantly shorter and narrower than seeded fruits, by 15% and 18%, respectively (FIG. 8), which is a significantly lighter fruit weight for seedless fruit. On average, seedless fruits were 38% lighter than seeded fruits.

In summary, for the winter growing trial (growing season from July to March), a significantly higher yield on seedless plants versus seeded plants was observed. Seedless plants produced smaller fruits but this was compensated for by the higher number of fruit. Thus, seedless plants yielded 9% more by weight than seeded plants due to an increase of 80% in fruit number.

What is claimed is:

1. A method for producing seed for growing a parthenocarpic seedless pepper plant comprising crossing as a female parent a first pepper plant comprising a cytoplasmic male sterile (CMS) trait with a second plant which is parthenocarpic to produce at least a first seed of a parthenocarpic seedless pepper plant, wherein the CMS trait is not a Peterson CMS trait, wherein the CMS trait is found in pepper line 09SP0004, and wherein a sample of seed of pepper line 09SP0004 was deposited under ATCC Accession No. PTA-12179.

2. The method of claim 1, further comprising harvesting said seed.

3. The method of claim 2, further comprising growing a parthenocarpic seedless pepper plant from said seed.

4. The method of claim 1, wherein the second pepper plant does not comprise a functional CMS restorer allele.

5. The method of claim 1, further comprising producing a population of seeds of a parthenocarpic seedless pepper plant.

6. The method of claim 5, wherein 100% of the population of seeds produces a seedless pepper plant.

7. The method of claim 1, wherein the parthenocarpic seedless pepper plant produces a fruit type selected from the group consisting of: bell pepper, pointed pepper, half long pepper, Como di Toro pepper, and Dulce Italiano pepper.

8. A seed produced by the method of claim 1.

9. A plant grown from the seed of claim 8, or a vegetative propagation thereof.

10. A plant part of the plant of claim 9, wherein the plant part comprises the CMS trait of claim 1.

11. The plant part of claim 10, further defined as a leaf, a bud, a meristem, an embryo, a root, a root tip, a stem, a flower, a fruit, or a cell.

12. The plant part of claim 9, further defined as a pepper fruit that lacks internal carpelloid structures.

13. The plant of claim 9, wherein the plant is a bell pepper plant.

14. A seedless pepper fruit, wherein the fruit is produced by a parthenocarpic seedless pepper plant grown from a seed prepared by crossing as a female parent a first pepper plant comprising a cytoplasmic male sterile (CMS) trait with a second plant which is parthenocarpic to produce at least said seed of a first seed of a parthenocarpic seedless pepper plant, wherein the CMS trait is found in pepper line 09SP0004, and wherein a sample of seed of pepper line 09SP0004 was deposited under ATCC Accession No. PTA-12179.

15. The seedless pepper fruit of claim 14, further defined as a bell pepper fruit.

16. A population of seedless pepper fruits according to claim 14, wherein at least about 80%, 90%, 95%, 99% or 100% of said population is made up of seedless pepper fruits.

17. The population of claim 16, wherein the population is defined as comprised of bell pepper fruits.

18. A method of producing a pepper plant comprising vegetatively propagating the plant of claim 9.

19. A tissue culture of regenerable cells of the plant of claim 9.

20. A population of seed produced by the method of claim 1, wherein 100% of the population of seed produces a seedless pepper plant.

21. The population of seed of claim 18, further defined as comprising at least about 25, at least about 50 or at least about 100 seeds.

22. The method of claim 1, wherein the CMS trait is obtained by combining, via backcrossing or by protoplast fusion, the cytoplasm of a *C. baccatum* plant with the nucleus of a *C. annuum* plant.

* * * * *